United States Patent
Roller et al.

(10) Patent No.: US 7,572,298 B2
(45) Date of Patent: Aug. 11, 2009

(54) IMPLANTABLE MEDICAL DEVICES AND METHODS FOR MAKING SAME

(75) Inventors: Mark B. Roller, North Brunswick, NJ (US); Yufu Li, Bridgewater, NJ (US); Jenny J. Yuan, Neshanic Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 1002 days.

(21) Appl. No.: 10/401,914

(22) Filed: Mar. 28, 2003

(65) Prior Publication Data

US 2004/0193285 A1 Sep. 30, 2004

(51) Int. Cl.
*A61F 2/62* (2006.01)
*A61F 2/28* (2006.01)

(52) U.S. Cl. .................. 623/23.75; 606/77

(58) Field of Classification Search ............ 606/60–61, 606/72–73, 77; 623/23.51, 23.75; 523/113, 523/115; 525/450, 937; 528/354; 524/414
See application file for complete search history.

(56) References Cited

U.S. PATENT DOCUMENTS

| | | | | |
|---|---|---|---|---|
| 3,991,750 | A * | 11/1976 | Vickery | 424/425 |
| 4,237,559 | A * | 12/1980 | Borom | 623/23.51 |
| 5,143,730 | A * | 9/1992 | Fues et al. | 424/426 |
| 5,308,623 | A * | 5/1994 | Fues et al. | 424/426 |
| 5,482,717 | A * | 1/1996 | Fues et al. | 424/426 |
| 5,509,913 | A * | 4/1996 | Yeo | 604/364 |
| 5,552,454 | A * | 9/1996 | Kretschmann et al. | 523/113 |
| 5,662,917 | A * | 9/1997 | Kim et al. | 424/422 |
| 5,725,541 | A * | 3/1998 | Anspach et al. | 606/151 |
| 5,747,390 | A * | 5/1998 | Cooper et al. | 442/59 |
| 5,955,529 | A * | 9/1999 | Imai et al. | 524/417 |
| 6,165,486 | A * | 12/2000 | Marra et al. | 424/423 |
| 6,331,313 | B1 * | 12/2001 | Wong et al. | 424/427 |
| 6,458,162 | B1 * | 10/2002 | Koblish et al. | 623/23.51 |
| 6,641,398 | B2 * | 11/2003 | Hagenbuch et al. | 433/223 |
| 6,752,834 | B2 * | 6/2004 | Geistlich et al. | 623/23.63 |
| 7,012,106 | B2 * | 3/2006 | Yuan et al. | 523/115 |
| 7,026,374 | B2 * | 4/2006 | Nathan et al. | 523/113 |
| 2002/0016636 | A1 * | 2/2002 | Ricci et al. | 623/23.51 |

(Continued)

FOREIGN PATENT DOCUMENTS

EP 0 441 537 A1 8/1991

(Continued)

OTHER PUBLICATIONS

European Search Report dated Jul. 29, 2004, for corresponding EP application 04251801.9.

*Primary Examiner*—Eduardo C Robert
*Assistant Examiner*—David Comstock
(74) *Attorney, Agent, or Firm*—Roberts Mlotkowski Safran & Cole, P.C.

(57) ABSTRACT

An implantable medical device is disclosed. The device is fabricated at least in part from a biocompatible, biodegradable composition. The composition is composed of a biocompatible, biodegradable polymer and a biocompatible, biodegradable wax. The concentration of the wax at the surface of the device is greater than the concentration of the wax in the body of the implantable device. The increased concentration of wax at the device surface may be attained when the device is heated to a temperature greater than the melting point of the wax and the glass transition temperature of the polymer, but lower than melting point of the polymer.

10 Claims, 4 Drawing Sheets

U.S. PATENT DOCUMENTS

| | | | |
|---|---|---|---|
| 2003/0040695 A1* | 2/2003 | Zhao et al. | 604/15 |
| 2003/0069326 A1* | 4/2003 | Stangel et al. | 523/113 |
| 2003/0120280 A1* | 6/2003 | Roller et al. | 606/77 |
| 2003/0233095 A1* | 12/2003 | Urbanski et al. | 606/72 |
| 2004/0001890 A1* | 1/2004 | Rosenblatt et al. | 424/469 |
| 2004/0006153 A1* | 1/2004 | Seppala et al. | 523/113 |
| 2004/0006385 A1* | 1/2004 | Valint et al. | 623/5.16 |

FOREIGN PATENT DOCUMENTS

| | | |
|---|---|---|
| EP | 0 558 965 A2 | 9/1993 |
| EP | 1 321 154 A2 | 6/2003 |
| WO | WO 93/15682 A1 | 8/1993 |
| WO | WO 01/44308 A2 | 8/2001 |

* cited by examiner

IMPLANTABLE MEDICAL DEVICES AND METHODS FOR MAKING SAME

FIELD OF THE INVENTION

The present invention relates to implantable medical devices fabricated at least in part from a composition containing a biocompatible, biodegradable polymer and a biocompatible wax and to methods of making such devices.

BACKGROUND OF THE INVENTION

Implantable medical devices have been widely used for more than 40 years in various surgical applications. For example, in the fracture fixation operations, medical devices are used to address bone fractures by attaching a reinforcing rod or a plate or a cage to a fractured bone so that the broken ends may be stabilized to promote fusion and consequent healing. In the sports medicine area, medical devices are used to repair and augment soft tissues, such as anterior cruciate ligament (ACL) replacement. Implantable medical devices such as screws are used to affix autografts, allografts, xenografts, or bone fragments to bone structure of a patient.

Though metals have long been used as implantable medical devices, biodegradable materials, materials that degrade in the body, and then either absorb into, or are excreted from, the body, have been used in as alternatives to metals. Specifically designed biodegradable materials can have mechanical properties that begin to approach those of bone in some applications. As healing progresses, the stiffness and strength of the biodegradable material implant gradually decrease, transferring loads from the implant to the healing bone tissue.

In medical procedures, the easy movement of a surface of a device with respect to tissue is important in reducing damage to both the surface and to the tissue. Damage to tissue as a result of "tissue drag" friction causes inflammation and pain to the patient and leads to a longer recovery time. Friction may also damage the material, thus rendering it ineffective or shortening its useful life.

The reduction of tissue drag using biodegradable and non-biodegradable polymers as coatings on medical devices has been widely reported. Some of the biodegradable polymers reported as coatings to reduce the tissue drag of medical devices include polymers, copolymers, and blends containing monomers of lactide, glycolide, epsilpon-caprolactone, trimethylene carbonate, para-dioxanone, ethylene oxide, and propylene oxide.

Many implantable medical devices, such as hip or knee prostheses, are structured such that there is movement of a surface of the device against another surface of the device. This surface-to-surface movement may occur during either implantation, or during the life of the device. The force resulting from the relative movement, or articulation, of one surface against another, is known as "device drag". In device drag, friction may damage the surface of the device, thus rendering it ineffective or shortening its useful life.

The issue of device drag in biodegradable and non-biodegradable implantable medical devices has been addressed in a variety of ways. Typically, low friction coefficient coating materials have been used to reduce device drag. Non-biodegradable coatings, such as ceramics or diamond like carbon, natural body fluids, or biodegradable polymers, have been reported as materials to coat on one or more of the contact surfaces to reduce friction between the surfaces.

Although considerable efforts have been applied to develop coating materials, there have been not many significant changes to the coating techniques for medical devices. The most often used coating techniques include spray coating, dip coating, wire coating, and powder coating. Although the mechanisms of these coating techniques are simple, the parameters involved are multiple.

For example, in spray coating, variables include the angle and the distance from the nozzle to the surface of the object, the opening of the nozzle, and the air pressure, all of which are key factors for the coating rate, which in turn determines the coating thickness. In addition, because of the uniqueness of medical device designs, custom-made device-specific gripping or holding systems are often required in the coating process. The use of the device-specific holding system requires the operators to periodically stop the coating process to remove coated objects and mount uncoated objects.

Another major aspect of the spray coating process is that organic solvents are widely used. The coating apparatus has to be placed in an environmentally safe location, which could make the cost of a simple coating process very expensive. In the case of medical devices formed from biodegradable polymers, a solvent must be chosen that does not adversely affect the polymer.

Finally, when a medical device is coated with a polymer, the performance of the coating is not only a function of the coefficient of friction of the coating material, but also of the interfacial bonding strength of the coating material and the device. Under high shear forces, the coating can delaminate from the device.

In summary, the problems of tissue drag and device drag in implantable medical devices have been of concern to the medical profession for some time. For medical devices formed from biodegradable polymers, both biodegradable and non-biodegradable coatings have been reported. However, the coating process is often complicated and involves solvents. Accordingly, there is a need for simpler methods of reducing tissue and device drag in biodegradable implantable medical devices.

SUMMARY OF THE INVENTION

The present invention is directed to an implantable medical device, the device containing a body and a first lubricated surface for contacting tissue, or a second surface of the device, or a surface of a second medical device, the implantable device fabricated at least in part from a biocompatible, biodegradable composition, the composition comprising a biocompatible, biodegradable polymer and a biocompatible, biodegradable wax, wherein the concentration of the wax at the first lubricated surface of the implantable device is greater than the concentration of the wax in the body of the implantable device, and to methods of making the device wherein the device is heated to a temperature greater than the melting point of the wax, greater than the glass transition temperature of the polymer, and lower than melting point of the polymer, thereby providing the lubricated surface.

DETAILED DESCRIPTION OF THE INVENTION

Tissue drag is a concern in fibrous medical devices such as suture, meshes, and other textiles. Device drag is a concern in medical devices where two articulating surfaces come together and need a certain lubricity to avoid wear and eventual failure of the device. The present invention provides biodegradable implantable medical devices fabricated at least in part from a composition that comprises a high molecular weight biocompatible, biodegradable polymer and a low molecular weight polymeric wax. For the purposes of this invention, a wax is defined as a substance that is solid at room temperature, low-melting, e.g. having a melting temperature of less than about 100° C., slippery, plastic when warm, and fluid when melted.

The devices of the present invention comprise a body encompassed by and constituted by exterior surfaces thereof, and a lubricated surface that contacts either a second surface of the device, or a surface of an additional device, or that contacts tissue when placed in the body. In order to reduce tissue and/or device drag, the lubricated surface comprises a greater concentration of the wax component than does the body of the device. The increased concentration of wax on the lubricated surface of the device is provided by heat treatment, i.e. annealing, of the device either during or after fabrication thereof as described herein. During the heat treatment, a portion of the wax component of the device migrates from within the body of the device to the surface of the device to act as a lubricant, thereby providing the lubricated surface. As such, a gradient of the wax material in the device is created, whereby the wax is more concentrated towards and on the lubricated surface than it is in the body of the device. Due to the increased concentration of wax on the lubricated surface, the devices reduce device and tissue drag without the presence of coatings conventionally used to accomplish the same results.

In order to possess bulk properties suitable for processing into medical devices, the compositions used to fabricate the devices preferably comprise a continuous, biodegradable polymer phase, with the biodegradable wax component initially being dispersed substantially homogenously there through. The individual components may be blended together such that the wax is homogeneously dispersed through the polymer phase. Such blends then may be further processed by standard methods of compounding, for example extrusion or batch compounding, followed by chopping of the compounded material to form pellets and the like of the homogenous blend. The pellets then may be used to prepare medical devices according to the invention, for example by extrusion or compression molding, where the fabrication of the medical device from the compounded compositions either includes or is followed by a heat treatment step according to the present invention.

Alternately, the individual components may be added directly to a compounding and molding apparatus, for example an extruder having the proper mixing screw configuration so as to homogenously blend the components in the extrusion barrel, with the extruder being fitted with the appropriate die and heating elements to form medical devices according to methods of the invention. Once having the benefit of this disclosure, one skilled in the art would be able to select the proper parameters and specific apparatus required for the particular blend of components and medical device being fabricated.

The continuous polymer phase comprises a high molecular weight, biocompatible, biodegradable polymer. High molecular weight polymers, as defined herein, comprise polymers with an inherent viscosity (IV) of greater than about 2.0 dl/g when measured in chloroform at 25° C. By biodegradable, it is meant that the polymer may be degraded or otherwise broken down in the body such that the components of the degraded polymer may be absorbed by or otherwise passed from the body.

Examples of suitable biocompatible, biodegradable polymers that could be used according to the present invention include, without limitation, polymers selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers, and copolymers and blends thereof.

Aliphatic polyesters useful according to the present invention include, but are not limited to, homopolymers and copolymers of lactide (which includes lactic acid, D-,L- and meso lactide), glycolide (including glycolic acid), epsilon-caprolactone, para-dioxanone (1,4-dioxan-2-one), trimethylene carbonate (1,3-dioxan-2-one), alkyl derivatives of trimethylene carbonate, monoglyceride polyesters, and polymer blends thereof.

Preferred polymers utilized in the invention comprise homopolymers of lactide (PLA) and homopolymers of glycolide (PGA). More preferred are copolymers of PLA and PGA (PLGA), such copolymers comprising from about 80 to about 99 mole percent PLA.

The wax component of the present invention is a low molecular weight biocompatible, biodegradable polymer with a low coefficient of friction. Low molecular weight polymers as defined herein comprise polymers with an Inherent Viscosity (IV) of less than about 0.7 dl/g when measured in chloroform at 25° C. Preferably, the IV is between about 0.3 and 0.5 dl/g when measured in chloroform at 25° C.

Examples of suitable biocompatible, biodegradable waxes that could be used include, without limitation low molecular weight polymers selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers, and copolymers and blends thereof.

Aliphatic polyesters which can be made into a wax, as defined herein, include, but are not limited to, homopolymers and copolymers of lactide (including lactic acid, D-,L- and meso lactide), glycolide (including glycolic acid), ε-caprolactone, para-dioxanone (1,4-dioxan-2-one), trimethylene carbonate (1,3-dioxan-2-one), alkyl derivatives of trimethylene carbonate, monoglyceride polyesters, and blends thereof.

For example, monoglyceride polyester (MGPE) materials suitable for this invention include biocompatible, biodegradable aliphatic polyester waxes made by the polycondensation of monoalkanoyl glycerides and common dicarboxylic acids These MGPEs have an aliphatic polyester backbone with pendant fatty acid ester groups and exhibit relatively low melting points, e.g. less than about 100° C. Preferred waxes preferably have a melting point of below about 80° C., more preferably from about 45° C. to about 60° C.

Among the preferred wax materials are copolymers of lactide (PLA) and glycolide (PGA) (PLGA); epsilon-caprolactone (PCL) and lactide (PCLA); and epsilon-caprolactone and para-dioxanone (PDO) (PCDO). A preferred wax material is a copolymer of 95 mole percent PCL and about 5 mole percent PDO (95/5 PCDO).

The most preferred wax material comprises a copolymer of epsilon-caprolactone and glycolide. This family of polymers is more fully disclosed in U.S. Pat. No. 4,994,074, issued Feb. 19, 1991, assigned to Ethicon Inc., which is hereby incorporated herein by reference as if set forth in its entirely. Most preferred are copolymers comprising about 90 mole percent epsilon-caprolactone (PCL) and about 10 mole percent glycolide (PGA) (90/10 PCGA).

Medical devices of the present invention also may comprise biocompatible, biodegradable inorganic fillers in order to provide reinforced implantable medical devices comprising a lubricated surface according to the present invention. Such fillers can be fine powders of ceramics comprising mono-, di-, tri-, α-tri-, β-tri-, and tetra-calcium phosphate, hydroxyapatite, fluoroapatites, calcium sulfates, calcium fluorides, calcium oxides, calcium carbonates, magnesium calcium phosphates, bioglasses, or mixtures thereof.

The biodegradable compositions used to prepare medical devices of the present invention can be used as a pharmaceutical carrier in a drug delivery matrix, or as a cell-based carrier in a tissue engineering application. To form the matrix, an effective amount of therapeutic agent can be added to the polymer or wax prior to, or during, the time of blending. The variety of different therapeutic agents that can be used in conjunction with the present invention is vast. In general, bioactive agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives such as rapamycin; muscle relaxants; parasympatholytics; psychostimulants; sedatives; tranquilizers; naturally derived or genetically engineered proteins, growth factors, polysaccharides, glycoproteins, or lipoproteins; oligonucleotides, antibodies, antigens, cholinergics, chemotherapeutics, hemostatics, clot dissolving agents, radioactive agents and cystostatics.

Growth factors include bone morphogenic proteins (i.e. BMPs 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I-III), and vascular endothelial growth factor (VEGF).

The polymer/wax blends used to prepare devices of the present invention can be melt processed by numerous methods to prepare a vast array of useful devices. These polymers can be injection or compression molded to make implantable medical devices for various surgical applications. The polymer/wax blends can be processed using solvent to prepare a vast array of useful devices. These polymer solutions can be cast into films and lyophilized into foams to make implantable medical devices for various surgical applications. Examples of medical devices of the present invention include, without limitation, reinforcing rods, plates, or cages to aid in the stabilization or fractured bone, and screws, pins, anchors, films, scaffolds, and expanding sleeve or collar devices to repair and augment soft tissues or affix autografts, allografts, xenografts, or bone fragments to the bone structure of a patient, each of which comprises a lubricated surface.

Figure 1:
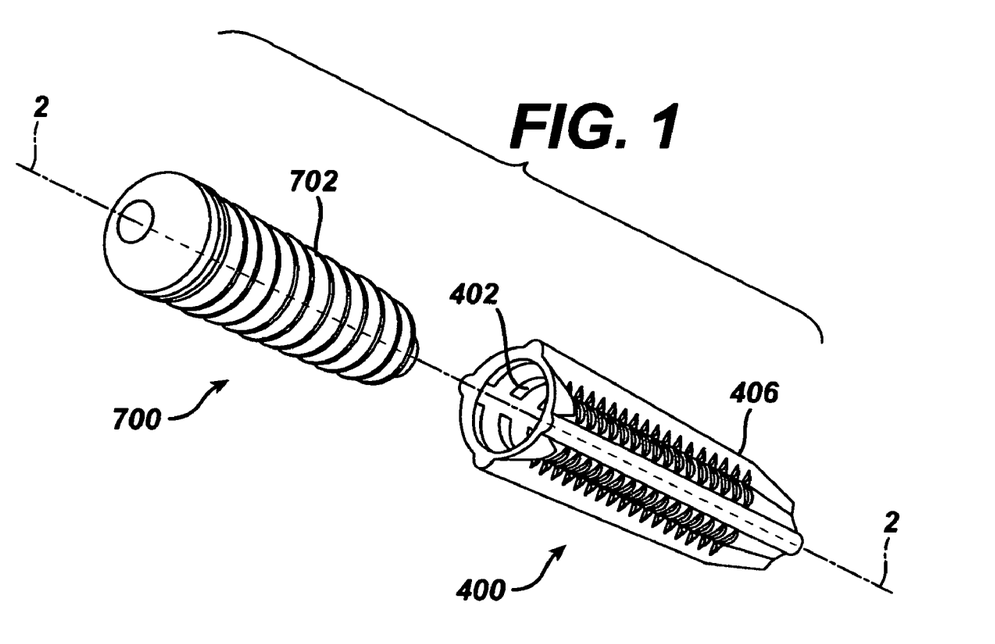
FIG. 1 is a perspective view of a biodegradable implantable medical device in accordance with one embodiment of the invention.

FIG. 1 is an exemplary implantable medical device formed according to the present invention. The device is a biodegradable graft ligament anchor. The design of the anchor components are disclosed in U.S. patent application Ser. No. 09/966766, entitled "Graft Ligament Anchor and Method for Attaching a Graft Ligament to a Bone", filed Sep. 28, 2001, the disclosure of which is hereby incorporated herein by reference in its entirety.

Figure 1A:
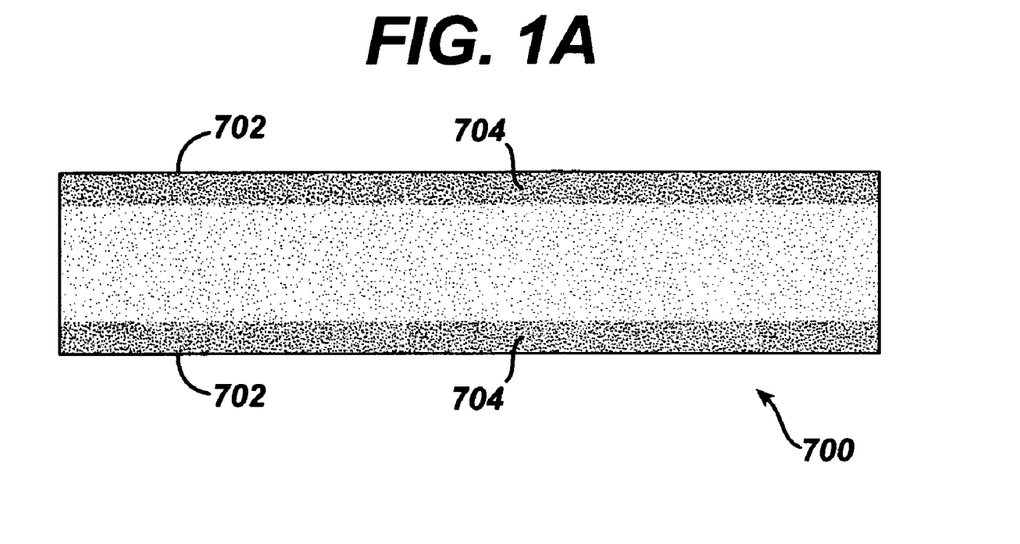
FIG. 1A is a perspective cross-sectional view of the medical device of FIG. 1 as seen along line 2-2.

The anchor comprises radially-expandable sheath 400 and sheath-expanding element 700. Expanding element 700 comprises lubricated surface 702 encompassing and constituting the body of expanding element 700. Radially-expandable sheath 400 comprises lubricated surfaces 402 and 406, also encompassing and constituting the body of sheath 400. During insertion, of expanding element 700 into radially-expandable sheath 400, the lubricated surface of sheath-expanding element 700 drags along inner lubricated surface 402 of radially-expandable sheath 400. Without lubricated surfaces 702 and 402, such drag may result in friction, which could cause damage to either or both surfaces of the anchor. As seen in FIG. 1A, biodegradable wax 704 has exuded to lubricated surface 702 of sheath-expanding element 700 following heat treatment according to the present invention, and acts as a lubricious coating to reduce the device drag and limit damage to surfaces 702 and 402. Reduced device drag reduces the insertion energy, measured in insertion torque, of an insertion tool (not shown) as it drives sheath-expanding element 700 into the central lumen of radially-expandable sheath 400.

Figure 2:
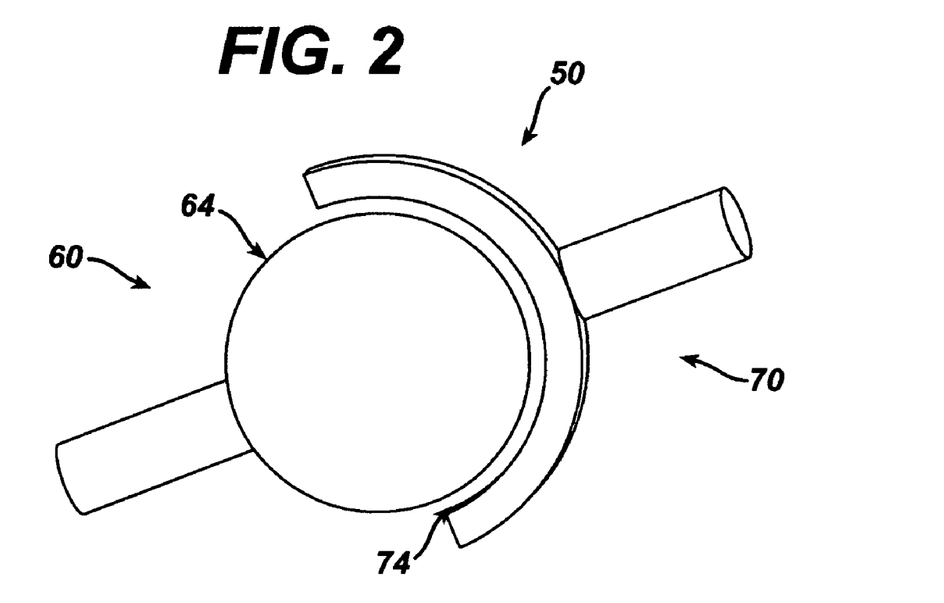
FIG. 2 is a cross-sectional view of a ball and socket component of a biodegradable implantable medical device in accordance with one embodiment of the invention.

FIG. 2 is a second exemplary implantable medical device formed according to the present invention. The device is a biodegradable ball and socket component 50 of a biodegradable implantable medical device. Ball and socket component 50 comprises a ball element 60 and a socket element 70. Socket element 70 has inner surface 74, while ball element 60 has outer surface 64. During function of ball and socket component 50, outer surface 64 of ball element 60 articulates against inner surface 74 of socket element 70. This articulation may result in device drag, which could cause damage to either or both surfaces 64 and 74. The biodegradable wax that has exuded on the respective surfaces of the device following annealing according to the present invention acts as a lubricious coating on either or both surfaces 64 and 74, thus reducing the device drag and limiting damage to the surfaces.

In order to prepare medical devices of the present invention, methods are provided that include a heat treatment step whereby a portion of the wax component of the device migrates to the surface of the device to act as a lubricant on the surface of the device without the need for conventional coatings. The device will be heat is treated, i.e. annealed, at a temperature that is above both the melting temperature of the wax component and the glass transition temperature of the polymer component, and lower than the melting point of the polymer. If the polymer is non-crystalline, or if the device is to be heat treated to temperatures above the melting point of the crystalline polymer, the heat treatment may need to be performed under constraint to avoid deformation. Preferably, the heat treatment temperature will be at least 10° C. to 20° C. lower than the melting temperature of the polymer to avoid significant deformation or distortion of the geometry of the device. The actual annealing temperatures used, then, are dependant on the compositions of the components of the blend.

The heat treatment may be performed simultaneously with formation of the device. For example, injection molding into a heated mold which acts as the heat treatment means may provide the lubricated surface of the device. Alternately, and preferably, the device will be formed via conventional molding techniques, for instance extrusion or compression molding, and the fabricated device then annealed at appropriate temperatures.

Although not intended to limit the scope of the present invention, one possible combination of compositions used according to the present invention is provided below to demonstrate the relation between heat treatment temperature and the intrinsic material properties. For example, a blend may be made from PLA polymer with waxes comprised of PCL polymer or copolymers containing at least 65 mole percent of PCL. Generally, the melting point of a PCL homopolymer or a copolymer containing at least 65 mole percent PCL will be 60° C. or lower. The glass transition temperature and melting point of semi-crystalline PLA polymers will generally be between about 65° and 180° C., respectively. Therefore, the PLA/PCL blend may be heat treated at a temperature in the range of from about 70° C. to about 140° C., and preferably at a temperature in the range of from about 80° C. to about 120° C.

The following examples are illustrative of the principles and practice of this invention, although not limited thereto. Numerous additional embodiments within the scope and spirit of the invention will become apparent to those skilled in the art. In the examples, the polymers and monomers were characterized for chemical composition and purity (NMR, FTIR), thermal analysis (DSC) for Tg, Tm and % crystallinity, and molecular weight by I.V.

The NMR sample preparation consisted of dissolving 250 milligrams of material into 20 ml of $CDCl_3$. NMR analysis was performed on two 0.7 ml aliquots of this test solution. Inherent viscosities (I.V., in dL/g) of the polymers and copolymers were measured using a 50 bore Cannon-Ubbelhode dilution viscometer immersed in a thermostatically controlled water bath at 25° C. utilizing chloroform as the solvent at a concentration of 0.1 g/dL.

Example 1

Compounding a Blend of PLA Polymer and PCDO Copolymer

The polymer, poly(lactic acid) (PLA) with an I.V. of 2.4 dl/g, was obtained from Purac Biochem (Gorinchem bv, the Netherlands). The PCDO copolymer, obtained from Ethicon, Inc., Somerville, N.J., was a copolymer of poly(epsilon-caprolactone) (PCL) and poly(para-dioxanone) (PDO) with a mole ration 95/5 mole percent (95/5 PCDO). The I.V. of the copolymer was 1.5 dl/g.

The polymer and PCDO copolymer were dry premixed at a weight ratio of 91/9. An 18-mm co-rotation twin-screw extruder (Model micro 18 GL/35, American Leistritz Extruder Corp., Somerville, N.J.) was used in the compounding process. The dry premix mixture was fed to the extruder at a feed rate of 5 lbs/hr using a gravimetric feeder.

The compounding conditions, using a low to medium shear screw design, were as follows: 1) temperature profile from the hopper to die was 100, 195, 195, 195, 190, 190, 190° C., 2) screw speed was 150 rpm, 3) melt pressure about 900 psi, and torque about 65 percent. The extrudate was cooled using an air cooling conveyer, then pelletized and stored at room temperature under vacuum for future application. The resulting blend was 91/9 PLA/(95/5 PCDO).

Example 2

Compounding a Blend of PLA Polymer and PCDO Wax

The polymer, poly(lactic acid) (PLA) with an I.V. of 2.4 dl/g, was the same as that used in Example 1. The wax, obtained from Ethicon, Inc., Somerville, N.J., was a copolymer of poly(epsilon-caprolactone) (PCL) and poly(para-dioxanone) (PDO) with a mole ration 95/5 mole percent (95/5 PCDO). The I.V. of the wax was 0.5 dl/g. The polymer and wax were dry premixed at a weight ratio of 91/9. The same extruder as described in Example 1 was used in the compounding process. The dry premix mixture was fed to the extruder at a feed rate of 5 lbs/hr using a gravimetric feeder. The compounding conditions, using a low to medium shear screw design, were the same as followed in Example 1. The extrudate was cooled using an air cooling conveyer, then pelletized and stored at room temperature under vacuum for future application. The resulting blend was 91/9 PLA/(95/5 PCDO).

Example 3

Compounding a Blend of PLA Polymer and PCGA Wax

The PLA polymer was the same as used in Example 1. The wax, obtained from Ethicon, Inc., Somerville, N.J., was a copolymer of poly(epsilon-caprolactone) (PCL) and poly(glycolide) (PGA) with a mole ration 90/10 mole percent (90/10 PCGA). The I.V. of the wax was between 0.3 and 0.5 dl/g.

The polymer and wax were dry premixed at a weight ratio of 15/85, 9/91 and 5/95. The same extruder as described in Example 1 was used in the compounding process. The dry premix mixture was fed to the extruder at a feed rate of 5 lbs/hr using a gravimetric feeder.

The compounding conditions, using a low to medium shear screw design, were the same as Example 1, except the melt pressure was about 800 psi, and the torque was about 25 percent. The extrudate was cooled using an air cooling conveyer, then pelletized and stored at room temperature under vacuum for future application. The resulting blend was 85/15 PLA/(90/10 PCGA).

Example 4

Injection Molding Test Coupons

Flex testing coupons (ASTM M695) of neat PLA, and the blends compounded in Examples 1, 2, and 3, were injection molded using a 35-ton injection molding machine (Model NN35M 14, Niigata Engineering Company, Ltd., Itaska, Ill). The processing conditions for molding the 91/9 PLA/PCDO coupons were as follows: 1) temperature profile 390, 400, 400, 400° F. from rear to nozzle, 2) injection pressure 26,860 psi, 3) holding pressure 26,080 psi, 4) injection speed 200 mm/s, 5) total time of injection and holding 6 seconds, and 6) cooling time 25 seconds. To make the PLA and 85/15 PLA/

PCGA coupons, the temperature profiles and the processing pressures were slightly different.

Example 5

Heat Treatment (Annealing) of 85/15 PLA/PCGA

A compression molder (Model MTP 1401, Tetrahedron Associates Inc., San Diego, Calif.) was preheated to 100° C. A batch of 85/15 PLA/PCGA coupons made in Example 4 was placed on polyimide film (sold under the trade name KAPTON by E.I. duPont, Wilmington, Del.) on the bottom platen of the molder. Coupons were collected after 30 minutes and 60 minutes. A second batch of coupons was heat treated at 140° C. using the same heat treatment procedure. A third batch of coupons was heat treated in air at 100° C. for 60 minutes in an annealing oven (Model No. AGC-336G-MP2, Blue M, Nanuet, N.Y.).

The surfaces of the unannealed and annealed samples were examined by attenuated total reflectance—fourier transform infrared red (ATR-FTIR). The results are shown on FIG. 3. The results indicate that PCGA migrated to the surface. NMR was also used for analysis. The remnants of the surface material were collected from the KAPTON films that were directly in contact with the surface of the coupons during heat treatment. The NMR detected only PCGA in the collected surface materials.

Example 6

Heat Treatment (Annealing) of 91/9 PLA/PCDO

The same heat treatment (annealing) procedures as in Example 5 were used to heat treat the 91/9 PLA/PCDO coupons made in Example 4.

Figure 3:
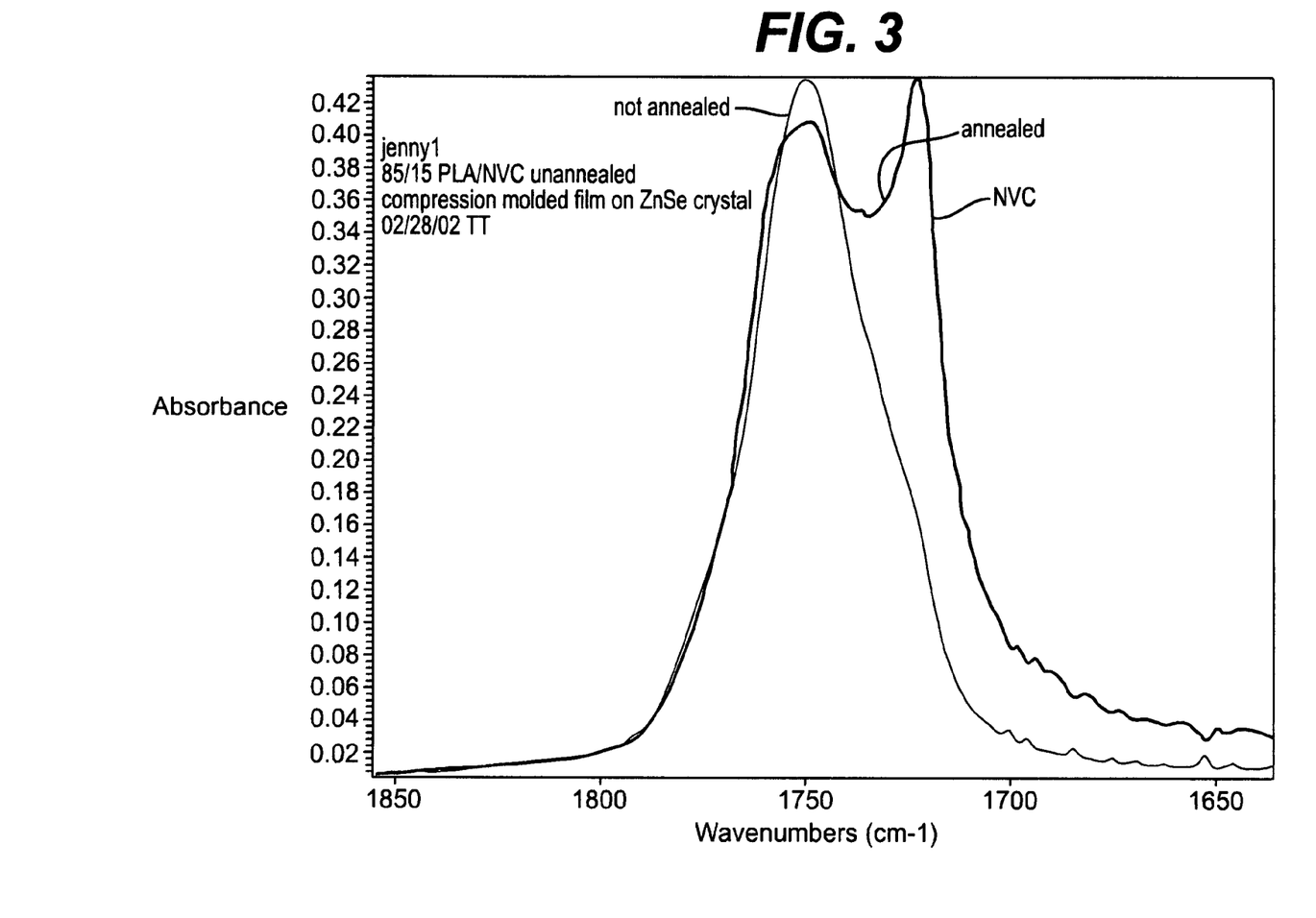
FIG. 3 is an attenuated total reflectance—Fourier transform infrared red (ATR-FTIR) plot of non-annealed and annealed 85/15 PLA/(90/10 PCGA) flex bars versus 90/10 PCGA film.
Figure 4:
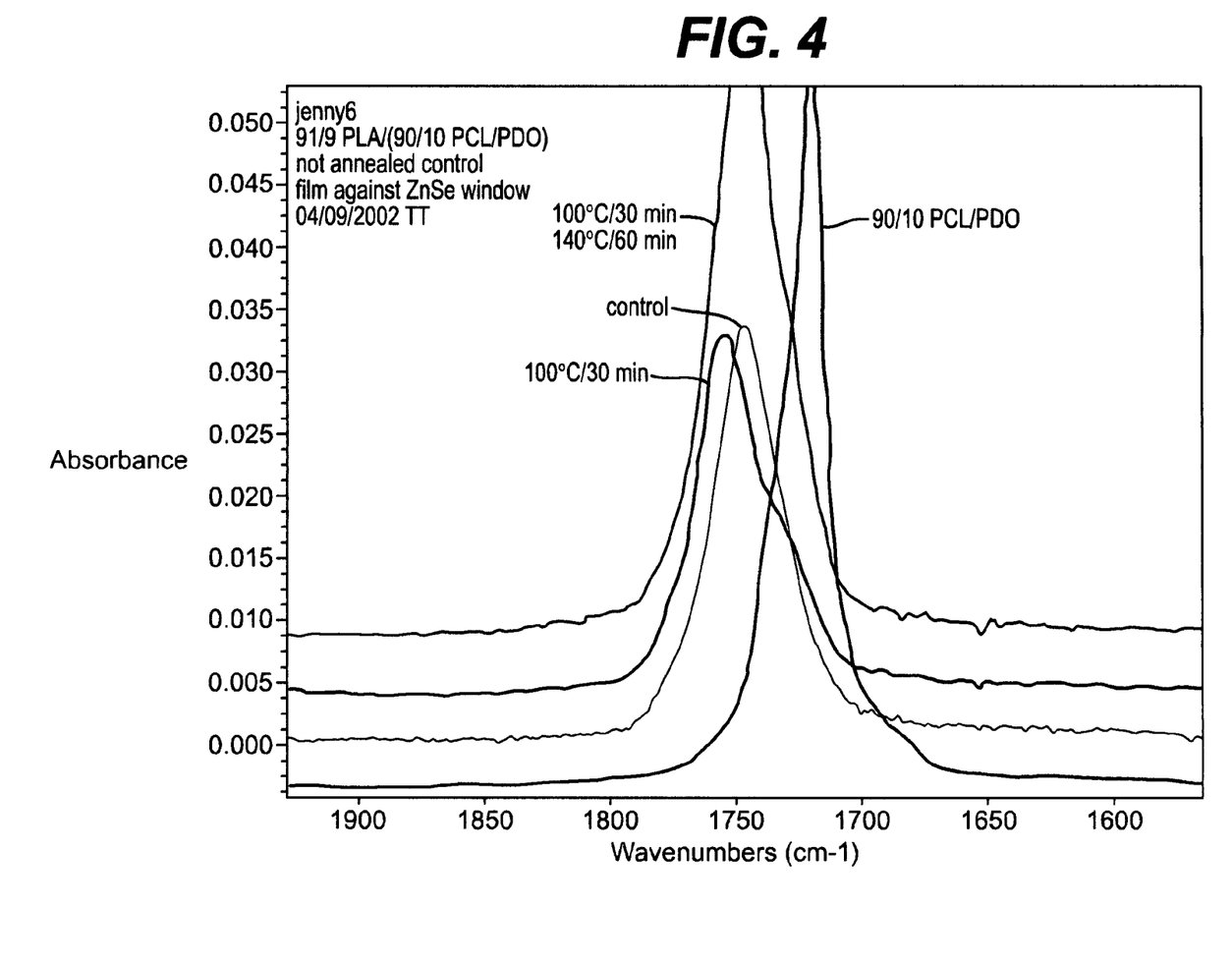
FIG. 4 is an ATR-FTIR plot of non-annealed and annealed 91/9 PLA/(90/10 PCDO) flex bars versus 90/10 PCDO film.

The surfaces of the unannealed and annealed samples were examined by ATR-FTIR, and the results for PLA/PCGA are shown on FIG. 3. The results indicate that during heat treatment the wax migrates to the surface. ATR-FTIR results shown in FIG. 4 are for the PLA/PCDO (where the PCDO IV is 1.5) blends molded and heat treated. The results show that the surface composition of the annealed coupons was the same as the unannealed coupons. There was no migration of PCDO toward the surface and no PCDO film formed on the surface. However, the I.V. of the PCDO copolymer was 1.5 g/dl, whereas the I.V. of the PCGA wax was between 0.3 and 0.5 dl/g. These results indicate that low molecular weight components can migrate towards the surface, while high molecular components cannot.

Example 7

Compounding a Blend of PLA Polymer, PCGA Wax, and Tricalcium Phosphate (TCP Filler)

The PLA polymer and PCGA wax were the same as those described in Example 3. The polymer and wax were premixed in a plastic bag with the weight ratio of 61 to 9. The same extruder as described in Example 1 was used in the compounding process. The dry premix mixture was fed to the extruder at a feed rate of 3.47 lbs/hr using a gravimetric feeder. Simultaneously, TCP powder (CAM Implants, Leiden, The Netherlands) was fed to the extruder at a feed rate of 1.53 lbs/hr from a second feeder.

The compounding conditions, using a low to medium shear screw design, were the same as Example 1, except the melt pressure was about 630 psi, and the torque was about 38 percent. The extrudate was cooled using an air cooling conveyer, then pelletized and stored at room temperature under vacuum for future application. The resulting blend was 30/61/9 TCP/PLA/(90/10 PCGA).

Example 8

Procedure for Forming an Exemplary Medical Device Using the Materials of the Present Invention Biodegradable graft ligament anchor components, as shown in FIG. 1, were manufactured using an injection molding process. The polymer used to manufacture the radially-expandable sheath elements was PLA (Purac Biochem (Gorinchem bv, the Netherlands), with an I.V. of 1.9 dl/g. The expandable sheath elements were formed using the PLA described in this example, the 91/9 PLA/PCDO formed in Examples 1 and 2, the 95/5, 91/9, and 85/15 PLA/PCGA blend formed in Example 3, and the 30/61/9 TCP/PLA/(90/10 PCGA) blend formed in Example 7.

All parts were injection molded using the 35-ton injection molder described in Example 4. For the PLA materials, the processing conditions were as follows: 1) temperature profile 390, 410, 430, 430° F. from rear to the nozzle, 2) injection pressure 18,370 psi, 3) holding pressure 16,700 psi, 4) injection speed 200 mm/min, 5) injection and holding time 2.5 seconds, and 6) cooling time 30 seconds.

For the 91/9 PLA/PCDO (where the IV of the PCDO was either 1.5 or 0.5) materials, the processing conditions were as follows: 1) temperature profile 350, 390, 410, 420° F. from rear to the nozzle, 2) injection pressure 21,400 psi, 3) holding pressure 21,000 psi, 4) injection speed 200 mm/min, 5) injection and holding time 2.5 seconds, and 6) cooling time 20 seconds.

For the 95/5, 91/9, and 85/15 PLA/PCGA materials, the processing conditions were as follows: 1) temperature profile 300, 370, 370, 380° F. from rear to the nozzle, 2) injection pressure 15,480 psi, 3) holding pressure 13,660 psi, 4) injection speed 200 mm/min, 5) injection and holding time 2.5 seconds, and 6) cooling time 13 seconds.

For the 30/61/9 TCP/PLA/(90/10 PCGA) materials, the processing conditions were as follows: 1) temperature profile 350, 390, 410, 420° F. from rear to the nozzle, 2) injection pressure 12,520 psi, 3) holding pressure 11,110 psi, 4) injection speed 200 mm/min, 5) injection and holding time 2.5 seconds, and 6) cooling time 20 seconds.

Example 9

Torque Forces Required to Engage the Graft Ligament Anchor Device of Example 8

The torque forces required to insert the sheath expanding elements into radially-expandable sheaths described in Example 8 were measured. The method was as follows: Pilot holes, 10 mm in diameter, were drilled in a model bone material (#25 Sawbone, Pacific Research, Vashon, Wash.). Four bovine tendons (8 mm diameter), from Frontier Medical, West Logan, Utah, were placed in each quadrant of the pilot hole to simulate hamstring tendons. A radially-expandable sheath was inserted inside the pilot hole so that the joint sealants were between the sheath and the walls of the pilot hole. The distal end of a sheath expanding element was inserted into the central lumen of the expandable sheath. A digital torque gauge (Digital Torque Gauge Model TMG, IMADA Incorporated, Northbrook, Ill.) was used to measure the insertion torque. The digital torque gauge was a driver connected to a torque meter so that the torque was measured while driving the sheath expanding element into the expandable sheath. The driver was disposed into the central cannulation of the sheath-expanding member.

The peak insertion torque values required to drive the PLA expanding element into the sheath central lumens are shown on Table 1.

TABLE 1

Insertion Torques

| Sheath Material | Torque (in-lb) |
| --- | --- |
| PLA | 30+ |
| 91/9 PLA/PCDO (PCDO IV = 1.5) | 30+ |
| 91/9 PLA/PCDO (PDCO IV = 0.5) | 12 |
| 95/5 PLA/PCGA | 30+ |
| 91/9 PLA/PCGA | 12 |
| 85/15 PLA/PCGA | 12 |
| 30/61/9 TCP/PLA/PCGA | 17 |

The results show that the sheaths formed of PLA, 91/9 PLA/PCDO (PDCO IV=1.5), AND 95/5 PLA/PCGA had little lubricity, while the sheaths formed of 91/9PLA/PCDO (PCDO IV=0.5), 91/9 PLA/PPCGA, 85/15 PLA/PCGA, and 30/61/9TCP/PLA/PCGA were lubricious. These results indicate that law molecular weight components, i.e., waxes, provide lubricious properties on the surface, while high molecular components cannot.

We claim:

1. An implantable medical device, comprising:
a body and a first lubricated surface for contacting tissue, or a second surface of said device, or a surface of a second medical device, the implantable device comprising a biocompatible, biodegradable composition, the composition comprising a biocompatible, biodegradable polymer having a glass transition temperature and a melting point and a biocompatible, biodegradable wax having a melting point, said biocompatible, biodegradable wax present in an amount greater than about 5% by weight, wherein:
 a) the wax is selected from the group consisting of homopolymers and copolymers of lactide, glycolide, epsilon-caprolactone, para-dioxanone, trimethylene carbonate, alkyl derivatives of trimethylene carbonate and monoglyceride polyesters having an inherent viscosity of less than about 0.7 g/dl as measured in chloroform at 25° C.; and
 b) the concentration of the wax at the first lubricated surface of the implantable device is greater than the concentration of the wax in the body of the implantable device and is achieved by heat treatment of the device at a temperature that is above the melting point of the wax and the glass transition temperature of the polymer and lower than the melting point of the polymer, thereby providing the lubricated surface.

2. The medical device of claim 1 wherein the biodegradable polymer is selected from the group consisting of aliphatic polyesters, poly(amino acids), copoly(ether-esters), polyalkylenes oxalates, polyamides, poly(ethylene glycol), poly(iminocarbonates), polyorthoesters, polyoxaesters, polyamidoesters, polyoxaesters containing amine groups, poly(anhydrides), polyphosphazenes, biopolymers and copolymers thereof.

3. The medical device of claim 2 wherein the aliphatic polyester is selected from the group consisting of homopolymers and copolymers of lactide, glycolide, epsilon-caprolactone, para-dioxanone, trimethylene carbonate, alkyl derivatives of trimethylene carbonate and monoglyceride polyesters.

4. The medical device of claim 3 wherein the aliphatic polyester comprises a copolymer of from about 80 to 99 mole percent lactide and glycolide.

5. The medical device of claim 4 wherein the aliphatic polyester has an inherent viscosity of greater than about 2.0 g/dl as measured in chloroform at 25° C.

6. The medical device of claim 1 wherein the wax comprises a copolymer of from about 90 to about 10 mole percent epsilon-caprolactone and glycolic acid.

7. The medical device of claim 1 further comprising an inorganic filler material.

8. The medical device of claim 7 wherein said inorganic filler material is selected from the group consisting of mono-, di-, tri-, α-tri-, β-tri-, and tetra-calcium phosphate, hydroxyapatite, fluoroapatites, calcium sulfates, calcium fluorides, calcium oxides, calcium carbonates, magnesium calcium phosphates and bio-glasses.

9. The medical device of claim 8 selected from the group consisting of reinforcing rods, plates, cages, screws, pins, anchors, expanding sleeves and expanding collars.

10. The medical device of claim 9 wherein the anchor comprises a radially-expandable sheath and a sheath-expanding element.

* * * * *